United States Patent
Callegaro et al.

(10) Patent No.: US 7,722,616 B2
(45) Date of Patent: May 25, 2010

(54) USE OF A BIOLOGICAL MATERIAL CONTAINING THREE-DIMENSIONAL SCAFFOLDS OF HYALURONIC ACID DERIVATIVES FOR THE PREPARATION OF IMPLANTS IN ARTHROSCOPY AND KIT FOR INSTRUMENTS FOR IMPLANTING SAID BIOLOGICAL MATERIAL BY ARTHROSCOPY

(75) Inventors: Lanfranco Callegaro, Thiene (IT);
Maurilio Marcacci, Bologna (IT);
Sergio Di Fede, Bologna (IT)

(73) Assignee: Fidia Advanced Biopolymers S.r.l., Abano Terme (IT)

( * ) Notice: Subject to any disclaimer, the term of this patent is extended or adjusted under 35 U.S.C. 154(b) by 0 days.

(21) Appl. No.: 10/250,408

(22) PCT Filed: Dec. 27, 2001

(86) PCT No.: PCT/EP01/15341

§ 371 (c)(1),
(2), (4) Date: Jun. 27, 2003

(87) PCT Pub. No.: WO02/053201

PCT Pub. Date: Jul. 11, 2002

(65) Prior Publication Data

US 2004/0044416 A1   Mar. 4, 2004

(30) Foreign Application Priority Data

Dec. 28, 2000 (IT) .................... MI2000A2845
Apr. 12, 2001 (IT) .................... PD2001A0090

(51) Int. Cl.
*A61F 5/00* (2006.01)
*A61F 2/02* (2006.01)
(52) U.S. Cl. ................... 606/86 R; 623/23.76

(58) Field of Classification Search .......... 123/18.11, 123/19.11, 19.12, 20.14, 20.17, 20.21; 623/11.11, 623/13.11, 16.11, 20.15, 20.16, 23.76, 23.74, 623/23.71, 23.72; 424/422, 423; 435/343
See application file for complete search history.

(56) References Cited

U.S. PATENT DOCUMENTS 4,851,521 A * 7/1989 della Valle et al. ......... 536/55.1

(Continued)

FOREIGN PATENT DOCUMENTS

WO   WO 99/65534   12/1999

(Continued)

OTHER PUBLICATIONS

J. Aigner, J. Tegeler, P. Hutzler, D. Campoccia, A. Pavesio, C. Hammer, E. Kastenbauer, A. Naumann, "Cartilage tissue engineering with novel nonwoven structured biomaterial based on hyaluronic acid benzyl ester," 1998, John Wiley and Sons, Journal Biomedical Material Research, vol. 42, pp. 172-181.*

(Continued)

*Primary Examiner*—Anu Ramana
(74) *Attorney, Agent, or Firm*—Clark & Elbing LLP

(57) ABSTRACT

The invention relates to use of a biological material containing cells supported on three-dimensional scaffolds containing at least one hyaluronic acid derivative for the preparation of grafts suitable for application by arthroscopy, and a kit of surgical instruments for implanting said biological material by arthroscopy.

11 Claims, 7 Drawing Sheets

U.S. PATENT DOCUMENTS

| | | | |
|---|---|---|---|
| 5,623,987 A * | 4/1997 | Golben et al. | 165/104.12 |
| 5,736,372 A * | 4/1998 | Vacanti et al. | 435/180 |
| 5,755,791 A * | 5/1998 | Whitson et al. | 623/1.1 |
| 5,769,899 A * | 6/1998 | Schwartz et al. | 606/77 |
| 5,842,477 A * | 12/1998 | Naughton et al. | 128/898 |
| 5,885,829 A * | 3/1999 | Mooney et al. | 435/325 |
| 5,919,196 A | 7/1999 | Bobic et al. | |
| 5,921,987 A | 7/1999 | Stone | |
| 6,027,743 A * | 2/2000 | Khouri et al. | 424/423 |
| 6,060,306 A * | 5/2000 | Flatt et al. | 435/297.2 |
| 6,224,630 B1 * | 5/2001 | Bao et al. | 623/17.16 |
| 6,333,029 B1 * | 12/2001 | Vyakarnam et al. | 424/93.1 |
| 6,378,527 B1 * | 4/2002 | Hungerford et al. | 128/898 |
| 6,454,811 B1 * | 9/2002 | Sherwood et al. | 623/23.76 |
| 6,530,956 B1 * | 3/2003 | Mansmann | 623/18.11 |
| 6,596,296 B1 * | 7/2003 | Nelson et al. | 424/426 |
| 6,835,377 B2 * | 12/2004 | Goldberg et al. | 424/93.7 |
| 2002/0009805 A1 * | 1/2002 | Nevo et al. | 435/366 |
| 2002/0045940 A1 * | 4/2002 | Giannetti et al. | 623/11.11 |
| 2004/0028655 A1 * | 2/2004 | Nelson et al. | 424/93.2 |
| 2004/0044416 A1 * | 3/2004 | Callegaro et al. | 623/23.76 |

FOREIGN PATENT DOCUMENTS

| | | |
|---|---|---|
| WO | WO 00/09179 | 2/2000 |
| WO | WO 00/37124 | 6/2000 |

OTHER PUBLICATIONS

Marcacci et al., "Arthroscopic Autologous Condrocyte Transplantation: Technical Note," Knee Surg, Sports Traumatol, Arthrosc 10:154-159, 2002.

* cited by examiner

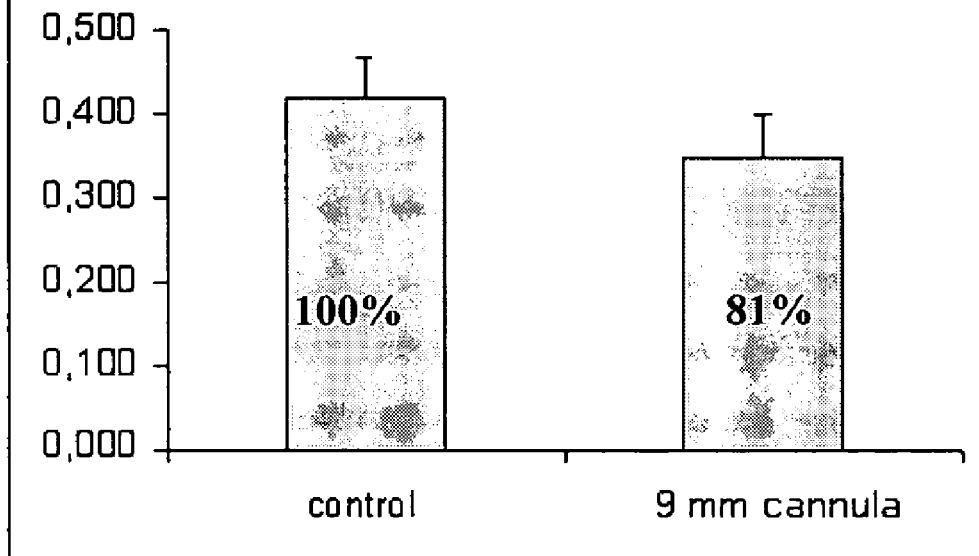
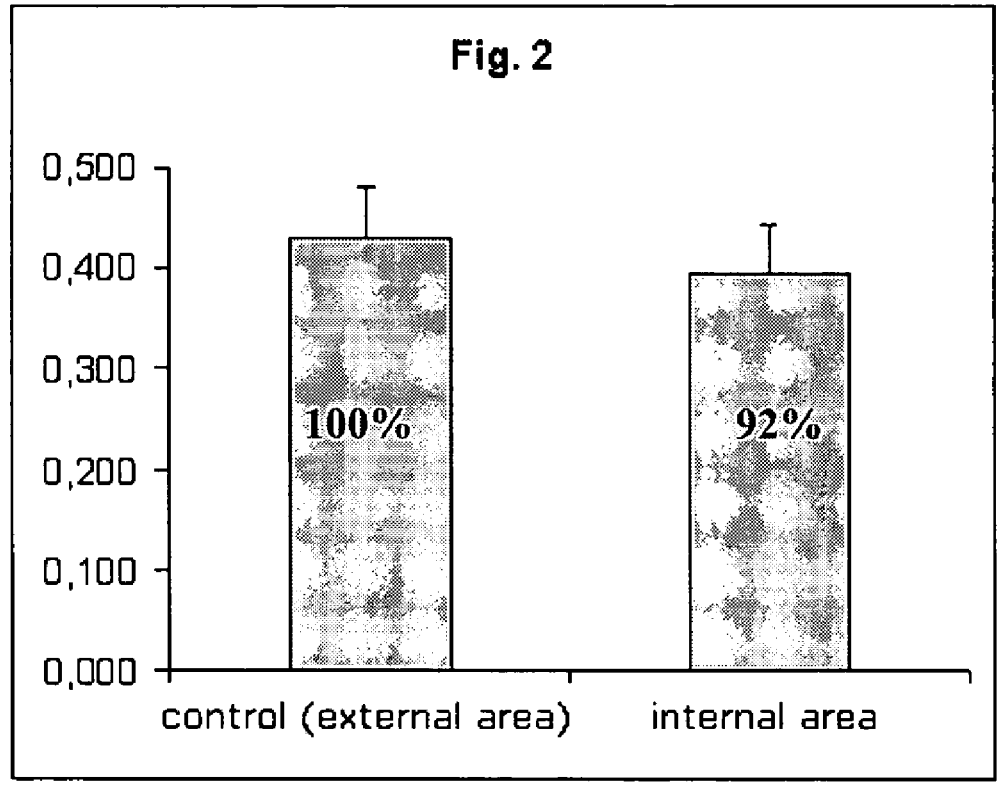

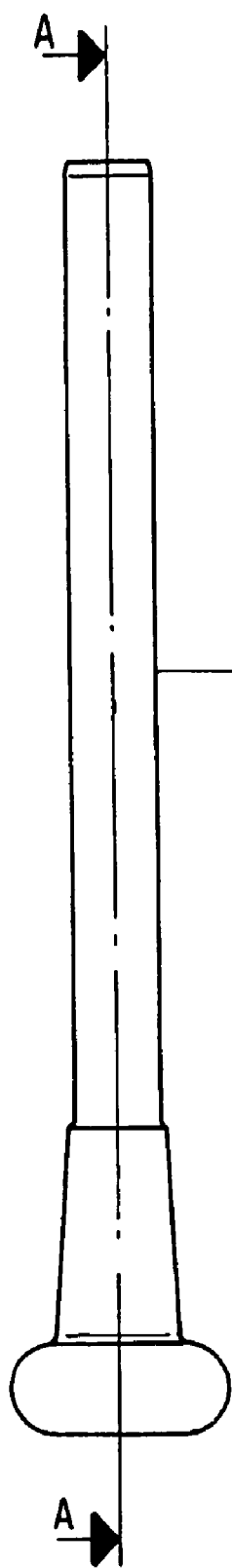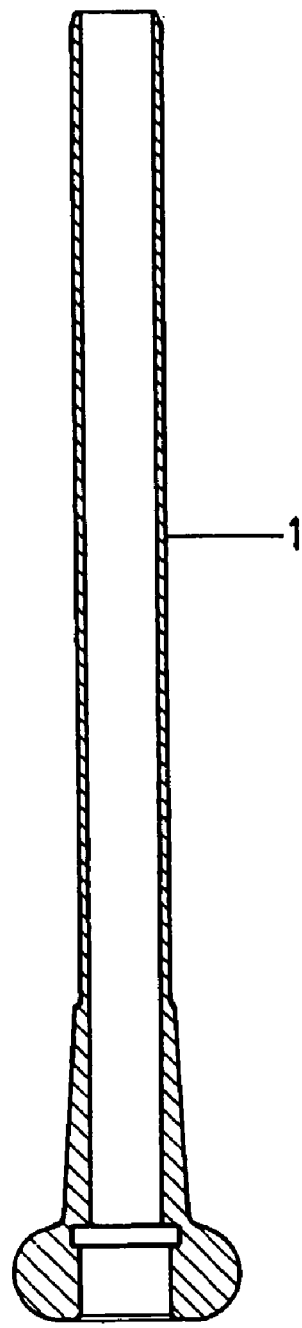
Fig. 3 (I)         Fig. 3 (II)

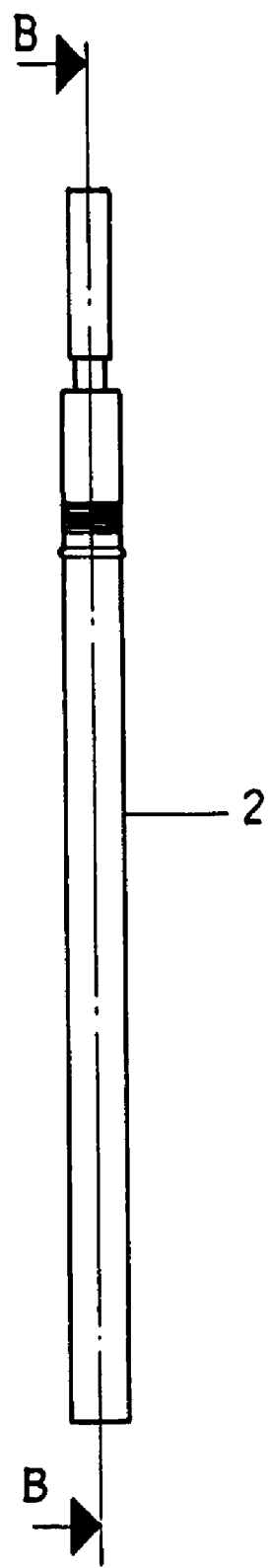
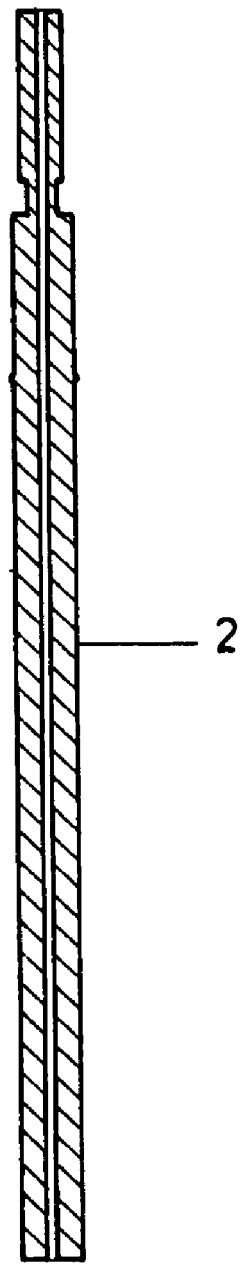
Fig. 4 (I)
Fig. 4 (II)

FIG. 5(I)
FIG. 5(II)
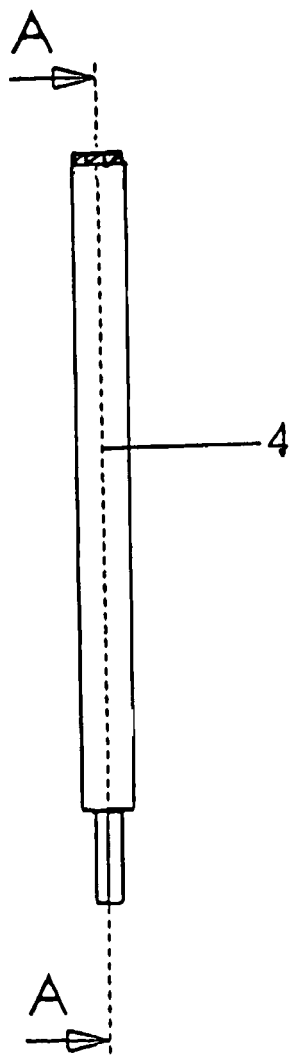
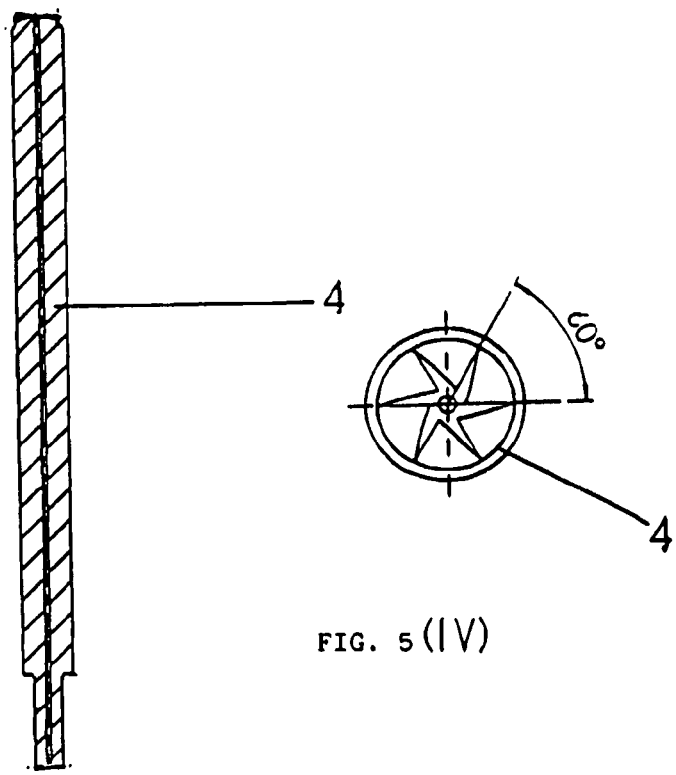
FIG. 5(IV)
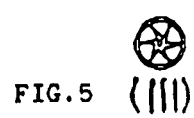
FIG. 5(III)

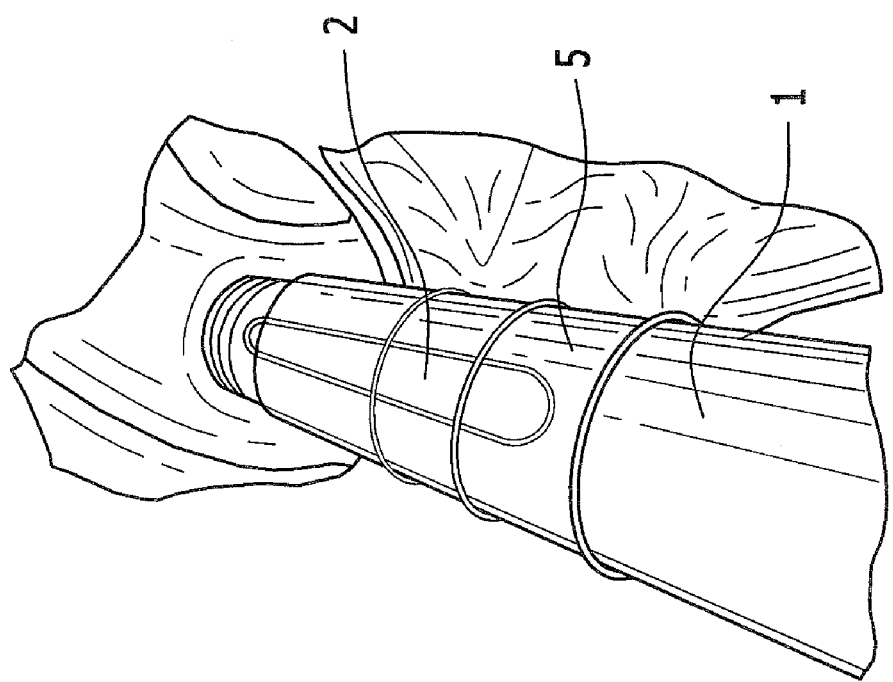
Fig. 6 (II)
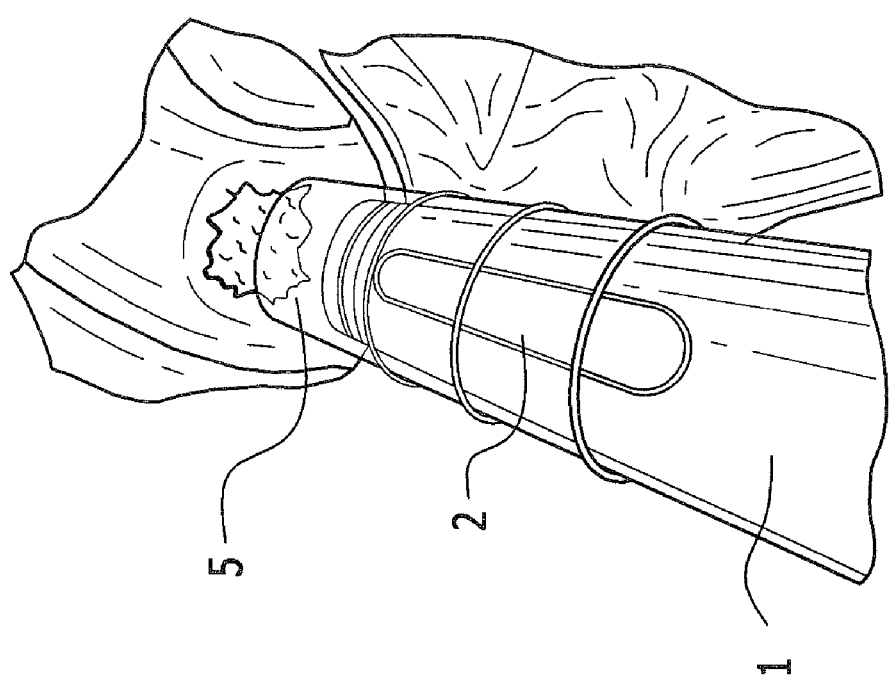
Fig. 6 (I)

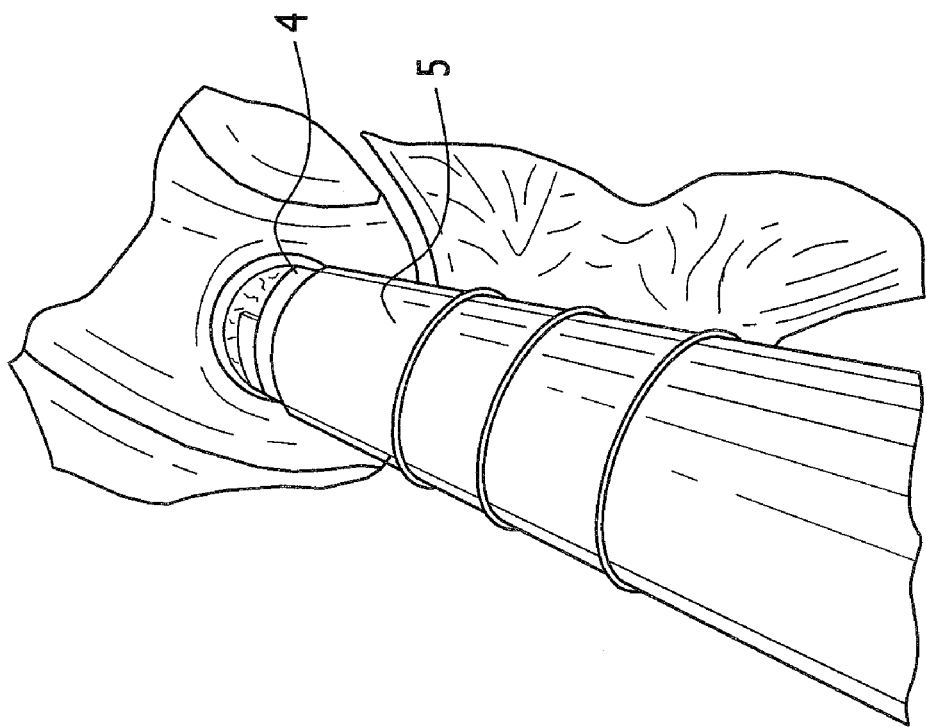
Fig. 7 (II)
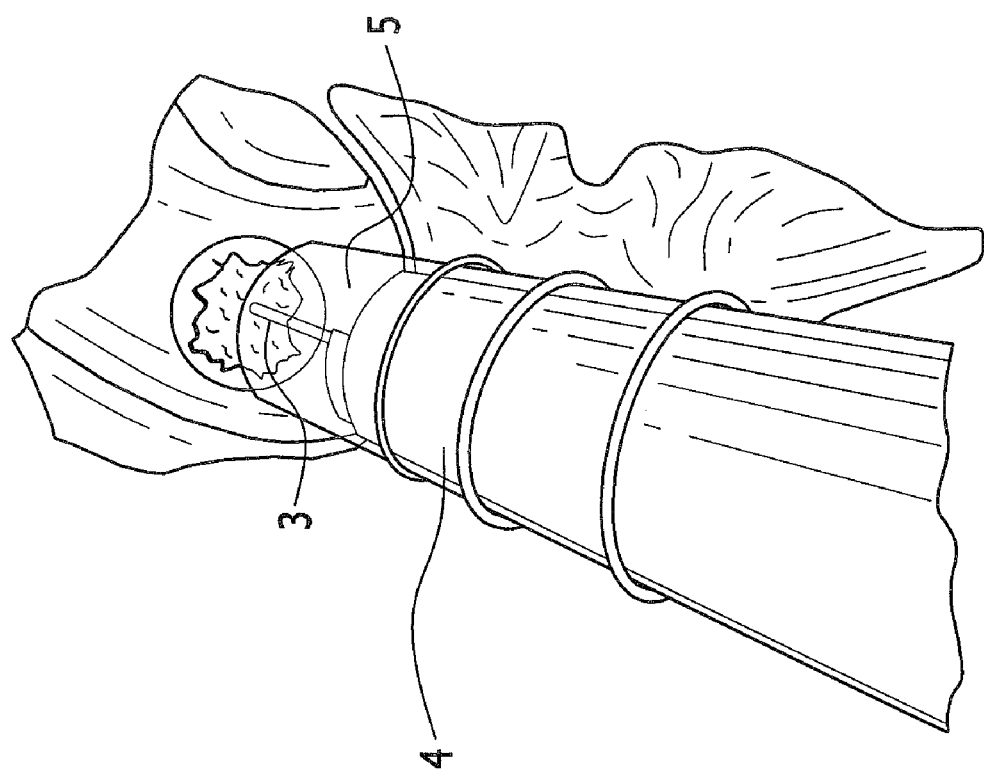
Fig. 7 (I)

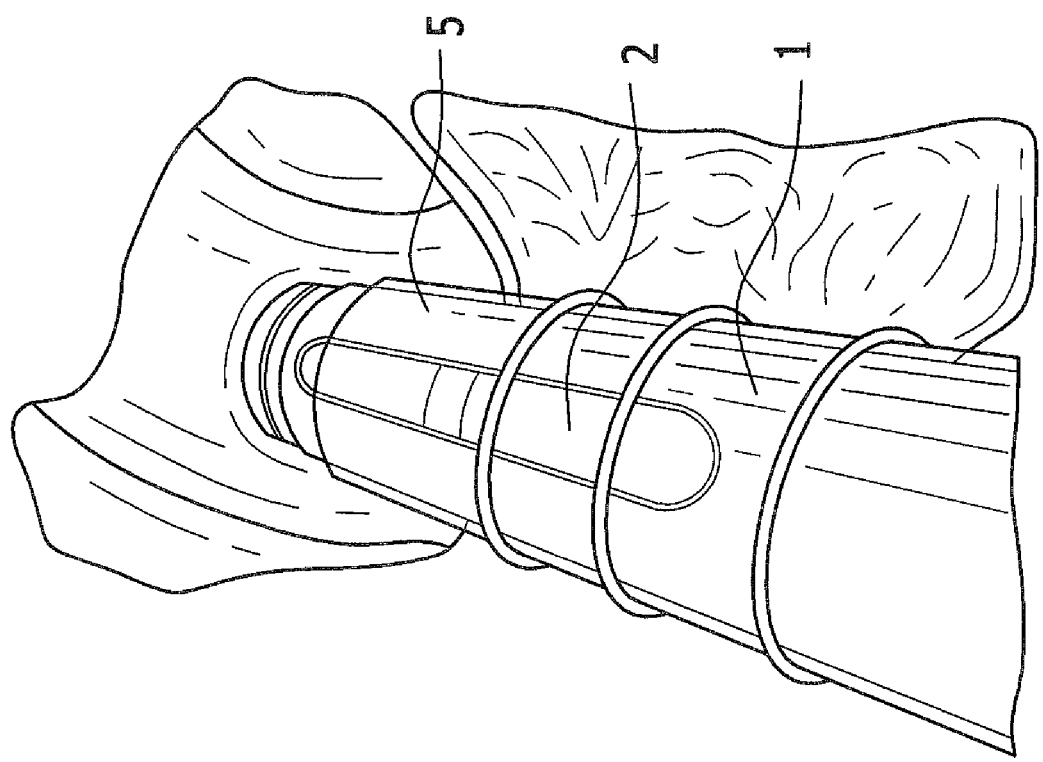

USE OF A BIOLOGICAL MATERIAL CONTAINING THREE-DIMENSIONAL SCAFFOLDS OF HYALURONIC ACID DERIVATIVES FOR THE PREPARATION OF IMPLANTS IN ARTHROSCOPY AND KIT FOR INSTRUMENTS FOR IMPLANTING SAID BIOLOGICAL MATERIAL BY ARTHROSCOPY

FIELD OF THE INVENTION

The present invention concerns the use of biological material containing cells supported on three-dimensional scaffolds which comprise at least one hyaluronic acid derivative for the preparation of grafts suitable for application by arthroscopy, and a kit for surgical instruments for implanting said biological material by arthroscopy.

BACKGROUND OF THE INVENTION

The aim of joint cartilage repair is to restore the integrity of the joint surface, reduce pain and prevent any further deterioration of the tissues.

Joint cartilage is a tissue which allows virtually frictionless movement of the joint. Its particular biological characteristics enable the joint to absorb forces at least five times greater than the body's weight. The joint cartilage, or hyaline, has a very limited capacity for self-repair, so the type of cartilage that is spontaneously regenerated after damage does not possess the same characteristics as the original tissue. It is known as fibrocartilage and has no properties of lubrication or absorption of mechanical shock. The final phase of hyaline cartilage degeneration is accompanied by pain and limited mobility that may cause locking of the joint. In the long term, the degenerative process may even cause the onset of complications such as osteoarthritis. In the most severe cases, the joint, usually the knee, has to be replaced with a metal prosthesis. This is a costly procedure and is not even permanent because many prostheses have to be changed after about 10-15 years. For this reason, knee replacements are only performed as a last resort in patients of under 50 years old. Joint cartilage lesions are currently treated by arthroscopic surgical techniques chiefly aimed at reducing pain, slowing down the degeneration process and, whenever possible, repairing the damage. Many methods have been applied to date to treat cartilage defects, and each of them has certain disadvantages (T. Minas et al. "Current concepts in the treatment of articular cartilage defects", Orthopedics, June 1997, Vol. 20 No. 6). One such technique involves trimming the margins of the cartilage defect, in other words, débridement of the edges of the lesion by removing any necrotic or diseased tissue. The technique of stimulating the marrow consists in reaching areas of the subchondral bone tissue by abrasion or perforation, thus stimulating the formation of a fibrin clot containing pluripotent stem cells. The clot then differentiates and takes form, giving rise to fibrocartilage repair tissue. The resulting tissue does not, however, have the mechanical properties or physiological or structural characteristics of healthy, lasting joint cartilage.

Another technique consists in implanting a piece of periosteum or perichondrium tissue, taken for example from rib cartilage, into the defect. Initially, this treatment triggers the development of hyaline cartilage, but the repair tissue does not take easily to the surrounding healthy tissues, and subsequently becomes ossified. Recently, a team of Swedish researchers devised an ex-vivo technique of grafting autologous chondrocytes, where chondrogenic cells are isolated from a small cartilage biopsy, grown in vitro and then regrafted in the same subject (M. Brittberg, A. Lindahl, A. Nilsson: "Treatment of deep cartilage defects in the knee with autologous chondrocyte transplantation", N. Eng. J. Med: 1994, 331, 889-895). According to the authors, in the culture phase, the chondrocytes temporarily de-differentiate and multiply under stimulation by suitable growth factors. Once transplanted to the damaged area, they recover their phenotype memory and consequently re-differentiate into chondrocytes able to produce a hyaline-type cartilage matrix. The surgical procedure is actually rather complex. First of all, the operation requires open surgery. Moreover, the cartilage defect must be well located and covered by a lid of periosteum (taken in the course of the same operation). This must be fixed to the cartilage tissue with a watertight seal of suture and fibrin (autologous or allogenic), so as to create a chamber into which the autologous cell suspension can be injected. Indeed, if the chamber is not perfectly sealed, the cells will leak out again and the operation will have failed.

To summarise, the main disadvantages of this procedure are that the operation is difficult to perform, the technique is invasive and the implanted cells are not perfectly differentiated. Autologous and homologous osteochondral grafts involve techniques that are surgically invasive and complex and there is a risk of viral transmission with the latter.

Other attempts at reconstructing the joint cartilage consist in implanting synthetic scaffolds containing allogenic chondrocytes, and growth factors able to stimulate proliferation of the chondrocytes.

The most frequently used synthetic scaffolds are of collagen gel, polyanhydride, polyorthoester, polyglycolic acid and the copolymers thereof. The chief disadvantage of using said scaffolds is represented by an immune response directed towards the implanted material.

There are known chondrocyte cultures in gel-scaffolds constituted by agarose, hyaluronic acid, fibrin glue, collagen and alginate.

However, said cultures in gel do not provide suitable mechanical stability to remain adhered to the site and allow the reconstruction of the cartilage structure.

Moreover, chondrocyte cultures in substances such as fibrin dedifferentiate into cells that are apparently similar to fibroblasts.

Lastly, although the gels constituted by substances such as agarose induce chondrocyte redifferentiation, the use of this compound has not been approved for internal application in humans.

As previously described joint cartilage defects have also been treated with isolated chondrocyte suspensions in the absence of supporting scaffolds. It is thought, however, that chondrocytes lose their viability and/or do not remain in the defect, and that they form fibrocartilage or islets of cartilage immersed in fibrous tissue (U.S. Pat. No. 5,723,331).

To overcome this problem, the Applicant has devised injectable compositions containing chondrocytes or cells of bone marrow stroma dispersed in a matrix containing at least one hyaluronic acid derivative (PCT patent application, publication No. WO00/37124).

As is known, hyaluronic acid plays a vital role in many biological processes, such as tissue hydration, proteoglycan organisation, cell differentiation, proliferation and angiogenesis (J. Aigner et al. L. Biomed. Mater. Res. 1998, 42, 172-181).

Also known is the use of hyaluronic acid derivatives prepared as described in EP patent No. 0216453 B1 for the preparation of three-dimensional scaffolds in the form of non-woven fabrics, membranes, sponges, granules, microspheres, tubes, gauzes, for the in vitro growth of stem and mesenchymal cells (PCT patent application publication No. WO 97/18842), in the form of a nonwoven fabric associated with a perforated membrane for the growth in vitro of fibroblasts and keratinocytes (PCT patent application No. WO 96/33750 and in the form of a nonwoven fabric for the growth of chondrocytes (J. Aigner et al. L. Biomed. Mater Res. 1998, 42, 172-181).

SUMMARY OF THE INVENTION

The Applicant has now found, surprisingly, that it is possible to use to effect three-dimensional matrices based on hyaluronic acid derivatives as scaffolds for cellular material for implantation in patients at arthroscopy, and that the use of such matrices solves the above problems involved in arthroscopic techniques.

The use of biocompatible and bioresorbable three-dimensional matrices based on hyaluronic acid on which cells are grown represents a huge step forward in arthroscopic techniques. Indeed, the cells begin to differentiate into chondrocytes while they are still growing on the matrix, because of the three-dimensional stimulation and the presence of suitable growth factors. Cell differentiation with the production of abundant hyaline matrix then continues in the lesion after grafting.

The fact that the cells are already mounted, before implantation, on a three-dimensional scaffold with hyaluronic acid's known properties of biocompatibility and bioresorption eliminates the need for a periosteal flap to be sealed over the defect to form a watertight lid, because the only covering the defect requires is one that will hold the graft in place until it has taken to the surrounding cartilage tissue.

All that is required, therefore, is a fibrin sealant (autologous or allogenic), or another biological glue, for a limited length of time. The fact that there is no longer any need for a flap of periosteum represents another major advantage: the arthrotomy technique used in the Swedish model can be substituted with the less invasive and more economical arthroscopy.

Subject of the present invention is therefore the use of a biological material containing cells grown on three-dimensional matrices containing at least one hyaluronic acid derivative for the preparation of implantations suitable for application by the arthroscopic technique.

The present invention further relates to a kit of surgical instruments for implanting the aforementioned biological material, said kit comprising:
a) a sterilisation tray;
b) a cannula with relative sterile valves to be used as a guide to give access, during arthroscopy, to the set of instruments listed hereafter;
c) a mapper-sampler, constituted by a hollow, cylindrical tube, used to circumscribe the cartilage lesion by creating a circular imprint, and to take cartilage tissue in the same circular form and of the same dimension as the imprint;
d) a guide wire that is fixed with the aid of a drill to the centre of the lesion, to guarantee stability to the cutter during use;
e) a concave, hollow cutter-abrasor used to create, within the margins of the imprint made by the mapper-sampler, the site in which the bio-engineered cellular support will subsequently be implanted;
f) a hollow plunger to be introduced into the mapper-sampler to push the bio-engineered cellular support into the previously prepared lesion site.

BRIEF DESCRIPTION OF THE FIGURES

FIGS. 1 and 2 show the results of Examples 3 and 4 insofar as it concerns the recovery of cellular viability expressed as optical density respectively in the form of bar charts, where said optical density is reported on the co-ordinate at 470 nm expressed in absolute unit measured with a FLOW spectrophotometer.

FIG. 3(I) represents respectively a schematic lateral view FIG. 3(II) a schematic cross section view along A-A of the mappler sampler.

FIG. 4(I) represents respectively a schematic lateral view and FIG. 4(II) a schematic cross section view along B-B of the hollow plunger.

FIG. 5(I) represents respectively a schematic lateral view, FIG. 5(II) a schematic cross section view along A-A, FIG. 5(III) a frontal view and FIG. 5(IV) a schematic and enlarged (3:1) frontal view of the concave hollow cutter-abrasor.

FIGS. 6(I) and 6(II) show a schematic representation of the mapper-sampler, while creating an imprint around the lesion.

FIGS. 7(I) and 7(II) show a schematic representation of the cutter stabilised by the guide wire fixed to the centre of the lesion, while functioning.

FIG. 8 shows a schematic representation of the mapper-sampler complete with the plunger as it places the biological material comprising cells grown on a three dimensional scaffold that has previously been cut out by the cutter,

DETAILED DESCRIPTION OF THE INVENTION

Of all the hyaluronic acid derivatives that can be used in the three-dimensional scaffolds according to the present invention, the following are the ones of choice:

hyaluronic acid esters wherein part or all of the carboxy functions are esterified with alcohols of the aliphatic, aromatic, arylaliphatic, cycloaliphatic or heterocyclic series (EP 0216453 B1);

crosslinked esters of hyaluronic acid wherein part or all of the carboxy functions are esterified with the alcoholic functions of the same polysaccharide chain or other chains (EP 0341745 B1);

crosslinked esters of hyaluronic acid wherein part or all of the carboxy functions are esterified with polyalcohols of the aliphatic, aromatic, arylaliphatic, cycloaliphatic, heterocyclic series, generating crosslinking by means of spacer chains (EP 0265116 B1);

hemiesters of succinic acid or heavy metal salts of the hemiesters of succinic acid with hyaluronic acid or with partial or total esters of hyaluronic acid (WO 96/357207);

O-sulphated derivatives of hyaluronic acid (WO 95/25751) or N-sulphated derivatives of hyaluronic acid (WO 98/01973);

Quaternary ammonium salts, for example salts with tetrabutylammonium and phenyltrimethylammonium, of hyaluronic acid or the derivatives thereof chosen from the group formed by N-sulphated hyaluronic acid, O-sulphated hyaluronic acid, the hemiesters of succinic acid with hyaluronic acid, possibly partially salified with heavy metals;

O-sulphated or N-sulphated hyaluronic acid and the derivatives thereof covalently bound to polyurethane (WO 99/43728).

The present three-dimensional scaffolds may also contain an association of several kinds of hyaluronic acid derivatives, and may be in various forms, such as nonwoven fabric as described in U.S. Pat. No. 5,520,916, meshes according to patent No. EP216453B1, perforated membranes as described in EP462426B1 unperforated membranes as in EP 216453B1, and sponges as described in EP 216453B1.

Such matrices may also include associations of natural, semisynthetic or synthetic polymers.

Natural polymers that can be used according to the present invention are, for example, collagen, co-precipitates of collagen and glycosaminoglycans, cellulose, polysaccharides in the form of gels such as chitin, chitosan, pectin or pectic acid, agar, agarose, xanthane, gellan, alginic acid or alginates, polymannan or polyglycans, starch, natural gums.

The semisynthetic polymers may be, for example, chosen from the group consisting of collagen crosslinked with agents such as aldehydes or precursors of thereof, dicarboxylic acids or their halogenides, diamines, derivatives of cellulose, hyaluronic acid, chitin or chitosan, gellan, xanthane, pectin or pectic acid, polyglycans, polymannan, agar, agarose, natural gum and glycosaminoglycans.

Lastly, examples of synthetic polymers that can be used are polylactic acid, polyglycolic acid copolymers or derivatives thereof, polydioxanes, polyphosphazenes, polysulphonic resins, polyurethanes and PTFE.

The present three-dimensional scaffolds may also include pharmaceutically or biologically active ingredients, such as anti-inflammatory agents, antibiotics, growth factors, antimicotics, antimicrobial and antiviral agents.

The cells used to prepare the present biological material were chosen from chondrocytes, osteocytes, mesenchymal cells and stem cells.

The cell culture process used to make the biological material according to the invention is that described by Aigner et al, "Cartilage tissue engineering with novel unwoven structured biomaterial based on hyaluronic acid benzyl ester", J. Biomed. Mat. Res. 1998, 42(2), 172-181.

From seven days after seeding on the three-dimensional scaffold based on hyaluronic acid derivatives, and preferably after the fourteenth day, the biological material is ready to be grafted.

The present biological material may be reduced to the size of the cartilage defect with a packer as used in mosaicplasty during the actual grafting process, that is, during surgery immediately before introduction of the surgical instrument. Alternatively, the material can be passed through a cannula, an instrument that is commonly used in arthroscopy or by using the surgical instruments of the kit of arthroscopy further subject of the present invention.

The biological material according to the invention may also be used to prepare both autologous grafts and allogenic grafts suitable for application by arthroscopic techniques.

Another advantage of the present invention lies in the fact that said biological material can be cryopreserved in order to preserve its characteristics of cell viability ready for implantation to be performed at a future time.

The kit of instruments for implanting biological material to be used for arthroscopy according to the present invention was constructed using materials with the preferred characteristic listed below:

The cannula previously listed at item (b) used as a guide to give access in arthroscopy to the set of instruments listed hereafter and represented in FIGS. 6(I), 6(II), 8 (indicated with the number 5), is in Aise 316 steel and presents an inside diameter of 11.5 mm and is 111 mm long. In the aforementioned figures the sterile valves are not indicated.

The mapper-sampler previously listed at item (c), being used to circumscribe the cartilage lesion by creating a circular imprint and to cut out and remove a piece of cartilage tissue of the same shape and size, and represented in the FIGS. 3, 6(I), 6(II) and 8 (indicated with number 1) is a cannula in Aise 316 medical steel, 155 mm long, with an outer diameter of 10.5 mm and an inside diameter of 9 mm. The mappler sampler 1 in the kit according to the present invention is a hollow cylinder large enough to hold the plunger and is further characterised by having a concave tip like the mapper sampler and a control system by which the pressure exercised by the advancing plunger can be interrupted.

The guide wire previously listed at item (d), fixed with the aid of a drill to the centre of the lesion to stabilise the cutter during use, and represented in FIG. 7(I) (indicated with the number 3) has the diameter of 1 mm.

The concave hollow cutter-abrasor previously listed at item (e), used to create within the margins of the imprint left by the mapper 1 the site in which the biological material to be used in arthroscopy according to the present invention for subsequent grafting and represented in FIGS. 5 and 7(I) and 7(II) (indicated with 4) is in Aise 316 medical steel, is 162.5 mm long with an inside diameter of 1.2 mm and an outer diameter of 9.5 mm.

The blades of the cutter 4 are concave so that they produce convex surfaces. The hollow plunger previously listed at item (e) that is introduced into the mapper-sampler 1 to push the biological material to be used in arthroscopy according to the present invention into the previously prepared lesion site and represented in FIGS. 4, 6(I), 6(II) and 8, (indicated with the number 2), has a diameter of 5 mm is a hollow cylinder large enough to hold a guide wire and that it has a concave tip like the mapper.

The use of said instruments enables the following operative technique to be performed:

A) a pneumatic tourniquet is placed around the proximal area of the limb the lesion area is identified by arthroscopy,
B) a needle is used to identify a point of entry directly above the lesion,
C) the skin is cut with a scalpel and a cannula 5 is introduced through the point of entry, through which the mapper-cutter 1 will be introduced to make a circular imprint within the lesion, 9 mm in diameter (mapping operation);
D) through the mapper 1 passes the concave, hollow plunger 2, and into this is introduced, in turn, the guide wire of 1 mm diameter, fixed with the help of a drill to the centre of the imprint. This guide wire will serve to stabilise the subsequent cutting operation;
E) both the mapper 1 and the plunger 2 are removed and the concave cutter 4, of the same size as the mapper (1) used earlier, is introduced. Holding the cutter perpendicular to the lesion, the latter is shaped, stopping at the distal point marked on the cutter;
F) using the mapper-sampler 1, the biological material of the dimensions 'mapped' earlier containing cells grown on the bio-engineered, three-dimensional scaffold is prepared and introduced through the cannula (1) complete with its concave plunger 2, thus enabling the biological material to be applied to the lesion,
G) the hollow, concave plunger 2 pushes the scaffold out of the mapper 1 into the convex hollow of the lesion;
I) the joint is repeatedly flexed and straightened to check the stability of the graft,
J) The pneumatic tourniquet is released and the arthroscopic apparatus (optical and the cannula 5) is removed.

The kit according to the present invention may be used also for Implanting the three-dimensional scaffolds containing autologous and/or allogenic cells, which can be constituted by natural, semisynthetic or synthetic polymers, free from hyaluronic acid derivatives.

The natural polymers are chosen from the group formed by collagen, coprecipitates of collagen and glycosaminoglycans, cellulose, polysaccharides in the form of gels such as chitin, chitosan, pectin or pectic acid, agar, agarose, xanthane, gellan, alginic acid or alginates, polymannans or polyglycans, starch and natural gums.

The following are the semisynthetic polymers of choice: collagen crosslinked with agents such as aldehydes or precursors thereof, dicarboxylic acids or their halides, diamines, derivatives of cellulose, hyaluronic acid, chitin, chitosan, gellan, xanthane, pectin or pectic acid, polyglycans, polymannan, agar, agarose, natural gum and glycosaminoglycans.

The synthetic polymers are chosen from the group formed by polylactic acid, polyglycolic acid, the copolymers or derivatives thereof, polydioxanes, polyphosphazenes, polysulphonic resins, polyurethanes and PTFE.

Moreover, the three-dimensional scaffolds according to the present invention may contain, besides cells, pharmaceutically or biologically active substances such as anti-inflammatory agents, antibiotics, growth factors, antimicotic or antiviral agents, and they may be cryopreserved to preserve their characteristics of cell viability ready for subsequent grafting by arthroscopy using the set of instruments claimed hereafter.

The following examples are for illustrative purposes and do not limit the scope of the present invention.

EXAMPLE 1

Preparation of the Biological Material

The cell culture process is described in Brun et al., "Chondrocyte aggregation and reorganisation into three dimensional scaffolds", J. Biomed. Mater. Res. 1998, 46, 337-346. Cartilage tissue taken from a non-weight-bearing area marginal to the lesion is detached by treatment with type-II collagenase, and the cells thus obtained are seeded in dishes containing HAM's F12 medium supplemented with foetal calf serum, 1% streptomycin-penicillin, 1% glutamine and with the following trophic factors, each of which in a quantity ranging between 1 and 10 ng/ml: TGF β1, recombinant human EGF, recombinant human insulin and recombinant human bFGF.

The cells are grown in vitro from one to four serial passages, then seeded on HYALOGRAFT®C (a non-woven fabric based on HYAFF®11t—total benzyl ester of hyaluronic acid), at a cell density of between $0.5 \times 10^6$ and $4 \times 10^6$ cells/cm$^2$, and the culture medium described above. At each change of medium (2-10 ml every 48-72 hours) 50 µg/ml of ascorbic acid is added.

EXAMPLE 2

Valuation of Cell Viability by the MTT Test

Cell viability of the biological material is determined by incorporation of the vital MTT dye (F. Dezinot, R. Lang "Rapid calorimetric assay for cell growth and is survival. Modification to the tetrazolium dye procedure giving improved sensitivity and reliability" J. Immunol. Methods, 1986, 22 (89), 271-277). A solution prepared by dissolving 0.5 mg/ml of MTT in phosphate buffer, pH 7.2 (PBS) is added to the test material and placed in an incubator set at 37° C. for 4 hours. Once incubation is complete, the MTT solution is aspirated, the material washed several times with PBS, after which 5 ml of extracting solution constituted by 10% dimethylsulphoxide in isopropyl alcohol is added. After centrifugation, the absorbance of the supernatant is determined by a spectrophotometric reading at 470 nm.

EXAMPLE 3

Verification of Cell Viability Recovery After Passage Through a Cannula

The MTT test as described in Example 2 is used to verify cell viability recovery after passage through a cannula, an instrument commonly used in arthroscopy and used here to place the biological material.

The results are reported in FIG. 1, which shows cell viability recovery relative to a bio-engineered cartilage construction (Hyalograft®C, dimensions 2×2 cm), prepared as described in Example 1. After 72 hours in its packaging, that is, in conditions of maximum metabolic stress, the biomaterial was gently extruded through a cannula with a diameter of 9 mm. It was found that the passage through the hollow of the cannula does not modify the cell viability of the present material.

EXAMPLE 4

Verification of cell viability recovery after packing with a mosaicplasty packer Once again using the MTT test as described above in Example 2, the viability of a bio-engineered construction reduced to the desired dimensions with a packing instrument as used in mosaicplasty, thus mimicking the conditions in which bio-engineered material is reduced in size to fit a cartilage defect for grafting, that is, during surgery, immediately before its insertion with the surgical instrument.

In this experiment, a cellular construction was kept in its packaging until the expiry date of the product (72 hours), then divided into sections 9 mm In diameter with a packer used in mosaicplasty. The viability of the single pieces was normalised by surface unit, and compared with the residue biological material.

FIG. 2 shows the results of this experiment.

The cell viability tests described above demonstrated that the application by arthroscopy of the present material, that is, biological constructs that have reached their expiry deadline (72 hours) in conditions of maximum metabolic stress, does not influence their biological qualities. This is regardless of the type of surgical instrument used to reduce the material and the packaging conditions of the product.

The invention being thus described, it is clear that the materials and methods used can be modified in various ways. Such modifications are not to be considered as divergences from the spirit and purpose of the invention and any such modification which would appear evident to an expert in the field comes within the scope of the following claims:

The invention claimed is:

1. A method for the treatment of a cartilage lesion by implantation of a graft at the cartilage lesion site by arthroscopic techniques, said method comprising the steps of:
    preparing an autologous and/or allogenic graft comprising a biological material suitable for implantation by arthroscopic techniques, by
    growing autologous and/or allogenic cells chosen from the group consisting of chondrocytes, osteocytes, mesenchymal cells, and stem cells onto three-dimensional scaffolds, for a period of time of seven to fourteen days, wherein said scaffolds comprise at least one hyaluronic acid derivative that is an ester of hyaluronic acid, wherein part or all of the carboxy functions of said hyaluronic acid are esterified with alcohols of the arylaliphatic series;
    circumscribing the cartilage lesion by creating a circular imprint by means of a mapper-sampler;

cutting out and removing a piece of damaged cartilage tissue having the same size and shape as the imprint;

preparing the so obtained biological material for arthroscopic implantation by means of the mapper-sampler to the size and shape of said imprint;

introducing the so reduced biological material into a cannula and applying the same to the cartilage lesion site.

2. The method according to claim 1, further comprising the step of adding one or more pharmaceutically or biologically active ingredients onto said three-dimensional scaffolds before the step of growing said autologous and/or allogenic cells.

3. The method according to claim 1, further comprising the cryopreservation of the said biological material before the step of preparing it for arthroscopic implantation in order to preserve the characteristics of cell viability ready for grafts to be performed at a future time.

4. The method according to claim 1, wherein said three-dimensional scaffolds are in the form of a non-woven fabric.

5. The method according to claim 1, wherein said three-dimensional scaffolds comprise a total benzyl ester of hyaluronic acid.

6. The method according to claim 1, wherein said three-dimensional scaffolds further comprise one or more pharmaceutically or biologically active ingredients.

7. The method according to claim 1, wherein said three-dimensional scaffolds consist of an ester of hyaluronic acid, wherein part or all of the carboxy functions are esterified with alcohols of the arylaliphatic series.

8. The method according to claim 7, wherein said three-dimensional scaffolds consist of a total benzyl ester of hyaluronic acid.

9. The method according to claim 7, wherein said three-dimensional scaffolds are in the form of a non-woven fabric.

10. The method according to claim 7, wherein said three-dimensional scaffolds consist of an ester of hyaluronic acid, wherein part or all of the carboxy functions are esterified with alcohols of the arylaliphatic series.

11. The method according to claim 10, wherein said three-dimensional scaffolds consist of a total benzyl ester of hyaluronic acid.

\* \* \* \* \*